United States Patent
van der Laan et al.

(10) Patent No.: US 6,664,533 B1
(45) Date of Patent: *Dec. 16, 2003

(54) APPARATUS AND METHOD OF REMOTE GAS TRACE DETECTION

(75) Inventors: Jan E. van der Laan, Palo Alto, CA (US); David E. Cooper, Palo Alto, CA (US); Russell E. Warren, Union City, CA (US); Sylvie Carlisle, Union City, CA (US)

(73) Assignee: Gas Research Institute, Des Plaines, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/488,453

(22) Filed: Jan. 20, 2000

Related U.S. Application Data
(60) Provisional application No. 60/116,679, filed on Jan. 20, 1999.

(51) Int. Cl.[7] .................................. H01J 40/14
(52) U.S. Cl. .............. 250/222.2; 250/573; 356/437
(58) Field of Search .................. 250/222.2, 222.1, 250/573, 574, 576, 339.11, 339.12, 339.13; 356/437, 438, 440; 340/555–557, 632, 633

(56) References Cited

U.S. PATENT DOCUMENTS 4,594,511 A   6/1986  Cooper et al. ......... 250/339.13
5,572,031 A  11/1996  Cooper et al. .............. 250/343
5,637,872 A  * 6/1997  Tulip ....................... 250/338.5

* cited by examiner

Primary Examiner—Que T. Le
(74) Attorney, Agent, or Firm—Mark E. Fejer

(57) ABSTRACT

This specification discloses a method and apparatus for the mobile and remote detection of a gas, such as methane, in the atmosphere. The apparatus includes a TDL based Light Detection and Ranging (LIDAR) driven at carrier frequency lying within the absorption line of the gas. The apparatus also drives the TDL with a modulation frequency to generate upper and lower sidebands in the output of the TDL and with a low ramp frequency to sweep the output of the TDL across twice the width of the pressure-broadened absorption line of the gas, preferably the first overtone absorption line in the case of methane detection. The apparatus include reference and calibration cells or chambers, and includes a light collector and detectors to detect the quantity and modulation of the light that passes the reference or calibration cells and that is received by the apparatus after reflection back toward the apparatus from an uncooperative target. The apparatus further includes a signal processor that applies a derivative spectroscopy technique, such as frequency modulation spectroscopy or wavelength modulation spectroscopy, to determine the presence of the gas in the atmosphere.

22 Claims, 3 Drawing Sheets

APPARATUS AND METHOD OF REMOTE GAS TRACE DETECTION

This application claims the benefit of Provisional application Ser. No. 60/116,679 field Jan. 20, 1999.

FIELD OF THE INVENTION

This invention relates to the use of Light Detection and Ranging (LIDAR) to detect elements in the atmosphere remotely. More particularly, this invention relates to mobile use of modulated tunable diode lasers in order to sweep the laser wavelength through an absorption line of a gas such as methane in order to determine the presence of the gas in the atmosphere.

BACKGROUND

LIDAR systems operate somewhat like radar. LIDAR, however, directs laser light rather than radar waves at a particular target to detect the target. The laser light may be pulsed or relatively continuously generated, and it may be focused or collimated as desired to reach the desired end. Objects, particles, and gases can scatter and/or absorb the laser light. Thus, the measurement of the reflected light can provide information about the target or atmospheric constituents along the optical path. LIDAR data is derived by collecting the scattered (reflected) light with a telescope, which focuses the collected light onto a photodetector. The amount or intensity of the light thus detected can be processed to provide information about the object being scanned and the optical path through which the laser beam passes.

LIDAR systems have been used in the past for the mobile determination of the presence of particular gases, such as the presence of methane from a gas line leak, in the atmosphere. One such LIDAR system employs an Optical Parametric Oscillator (OPO) as the laser source. OPO based LIDAR is particularly effective for determining the presence of methane because the wavelength of the OPO-based light lies in the fundamental absorption band of the methane gas.

On the other hand, OPO-based LIDAR is expensive and also requires extreme environmental controls to maintain stable long term operation. OPO systems are complex and prone to alignment problems, requiring highly trained maintenance personnel.

Also, since OPO-based LIDAR emits pulses of laser light, the pulse repetition frequency (PRF) can present a significant problem for mobile applications seeking to detect small gas plumes, such as gas leak plumes. Most currently used commercial OPO-based systems having sufficient output energy to detect such plumes operate at a PRF of 10 Hz or less. At such extremely low pulse repetition rates, the speed of the mobile measurement platform can strongly influence the measured data. The mobile platform is thus not only likely to miss some plumes entirely but also can incorrectly estimate plume concentrations as the OPO is tuned between wavelengths and the target moves relative to the OPO-based system. Although the latter, moving-target problem can be reduced by using two OPO-based LIDARs that near simultaneously transmit differential wavelength pairs, this dual-OPO laser system is not only expensive but also very complex and does not solve the former, low PRF problem.

Recently, OPO-based systems have been developed that provide higher PRF rates (in the kHz range). One such system is that developed by Sandia National Laboratory. These systems, however, produce micro-joule energies due to the high PRF, requiring long integration times to accomplish detection. For this reason, the system will likely miss small or low concentration plumes, particularly in the mobile environment. These systems are also very expensive—probably too much so for use by pipeline survey companies—and they are difficult to maintain in alignment, especially in a mobile application. This is because OPO-based systems require extreme environmental controls and stability to operate properly. Field and mobile applications generally do not allow for these types of controls.

Another prior art LIDAR technique uses frequency mixing to generate emissions in the fundamental absorption band of methane. These frequency-mixing systems use expensive lasers (such as ND-YAG and Ti:Sapphire lasers in downconverting frequency mixing schemes or $CO_2$ lasers in upconverting devices). Like the OPO-based systems, they also are non-linear crystal based systems that are difficult to maintain in alignment, especially in mobile applications.

There are also Tunable Diode Lasers (TDLs) that have been developed for the detection of methane gas plumes in the atmosphere. One such TDL laser has been developed by the Tokyo Gas Company. The Tokyo Gas TDL laser is reported to have sufficient sensitivity to detect gas line leaks, using low frequency wavelength modulation and lock-in (phase differential) detection. Low frequency lock-in detection, however, has several major disadvantages for mobile, remote detection operations.

First, low frequency lock-in detection requires long scanning and data averaging times to achieve sufficient sensitivity to detect small remote plumes. As a result, low frequency lock-in detection TDL LIDAR techniques are effectively limited to static line-of-sight, not mobile, applications.

Second, although there are other processing techniques such as matched filtering that can often be used in LIDAR systems to improve sensitivity, these techniques cannot be used with low frequency TDL LIDAR systems. This is because these types of processing techniques are based on the absorption line signature information which require use of much higher (RF) frequencies.

While there are lasers available, such as the OPO-based LIDARs described above, that operate within the fundamental absorption level and overtone band of gases such as methane, the applicants believe that such systems have not provided a solution to the problem of using LIDAR to economically and reliably detect gas leaks, particularly methane gas leaks, in mobile applications.

There have been TDL-based lasers in the prior art that operate in the first overtone band, but not in the fundamental absorption band, of gases such as methane, but they have not been applied to mobile detection of gases such as methane. Because such lasers operate in only the overtone band, they are not as readily absorbed by gases such as methane. Applicants believe that, as a result of this limitation and possibly other aspects of TDL-based lasers, such lasers have not been applied to the mobile detection of gases such as methane.

Frequency Modulation Spectroscopy (FMS) techniques exist in the prior art, such as those identified in U.S. Pat. No. 4,594,511 ("the '511 Patent"), entitled "Method and Apparatus for Double Modulation Spectroscopy," issued to one of the present inventors, and in U.S. Pat. No. 5,572,031 ("the '031 Patent"), entitled Pressure and Temperature Compensating Oxygen Sensor, issued to two of the present inventors.

As the '511 Patent explains, FMS can be used to detect spectral properties of a sample more economically, conveniently, and accurately than detection techniques operating strictly in the frequency domain of the information of spectroscopic interest. The '511 Patent also states that such FMS techniques can be used to take measurements of gaseous samples.

Although the '511 patent does suggest that FMS techniques may be used with a variety of lasers including TDL-based lasers, the '511 patent does not teach how to apply FMS techniques to any particular TDL apparatus. The '511 Patent also does not teach any mobile apparatus or method or use of FMS or TDL techniques to detect methane gas in particular, much less remotely detect methane gas in the atmosphere.

BRIEF SUMMARY OF ASPECTS OF THE INVENTION

The applicants have invented a method and apparatus for remote detection of gas, preferably methane, dispersed into the atmosphere. The method utilizes a TDL-based LIDAR, utilizing a TDL whose frequency can be altered by changing the TDL drive current. The TDL laser is driven by a drive current or carrier, and the carrier frequency is preferably centered in the center of the absorption line of the gas in issue. A small RF modulation current (preferably at 4 MHZ) is superimposed on the TDL carrier frequency to produce sidebands, which lie within the pressure broadened absorption line of the gas. A low frequency (about 1 KHz) sawtooth ramp current is also superimposed on the TDL drive current to sweep the carrier and its associated sidebands over a range, and the range preferably is twice as wide as, and centered on, the atmosphere-pressure broadened absorption line width of the gas. The resulting TDL light is directed at an uncooperative target and collected by a detector. An uncooperative target is one which is undefined, such as a methane plume, rather than a defined target such as a retroreflector. The collected sideband laser light and carrier signal are then fed to an FMS processor to generate a derivative signature, preferably a second derivative signature (derived from the mixing of upper and lower sidebands) that indicates whether the gas is present in the atmosphere. A closely related technique, WMS, or wavelength modulation spectroscopy, can achieve comparable results in certain situations and may be used in some instances in place of FMS in the present invention.

The present method and apparatus preferably includes a reference WMS gas detection technique. The reference provides a baseline for comparison of the atmospheric derivative signature with the reference derivative signature and confirmation that any apparent detection of the gas in issue from the atmosphere derivative signature is consistent with the reference signature and not likely to be the result of misalignment, anomalous performance of the apparatus, or gas other than sought to be detected in the atmosphere.

It is to be understood that this is a brief summary of aspects of the invention. There are other aspects of the invention that will become apparent as the specification proceeds.

OBJECTS OR ADVANTAGES OF THE PRESENT INVENTION

It is therefore an object and an advantage of the present invention to provide an apparatus and method for mobile detection of gas leaks in the atmosphere, particularly methane gas leaks.

It is an advantage of the present invention to provide a LIDAR (and method of using it) that is relatively sensitive, mobile, and economical.

It is yet another advantage of the present invention to provide a LIDAR that is relatively stable and rugged, and can operate unattended or with relatively minimal attention by an operator.

It is a further advantage of the present invention to provide a relatively compact LIDAR for detection of gas plumes.

It is a still further advantage of the present invention to incorporate commercially available TDL's to achieve the mobile detection of gas plumes in the atmosphere.

It is an additional advantage of the present invention to provide a mobile gas detection LIDAR that utilizes a single source emitter.

Another advantage is that the present invention provides continuous wave operation, reducing the likelihood of missing the detection of a remote gas line leak when the apparatus is moving.

It is yet another advantage of the present invention to provide a gas detection technique that not only is mobile but also provides for self-calibration through the gas detection process.

A further advantage is that the present invention includes a reference gas detection signature to compare against an apparent detection of gas in the atmosphere and ensure that the apparent detection is correct.

A still further advantage of the invention is that it can use an TDL laser that emits light in other than the primary absorption band of the gas under study and yet detect the gas.

There are other objects and advantages of the present invention. They will become apparent as the specification proceeds.

In this regard, it is to be understood that, although the applicants' believe that their preferred embodiment described herein meets the objects and provide the advantages recited herein, the scope of the invention is to be determined by reference to the claims and not necessarily by whether any given embodiment achieves all objects and advantages stated herein.

BRIEF DESCRIPTION OF THE DRAWINGS

The applicants' preferred embodiment of the present invention is shown in the accompanying drawings in which.

DESCRIPTION OF THE PREFERRED EMBODIMENT

Figure 1:
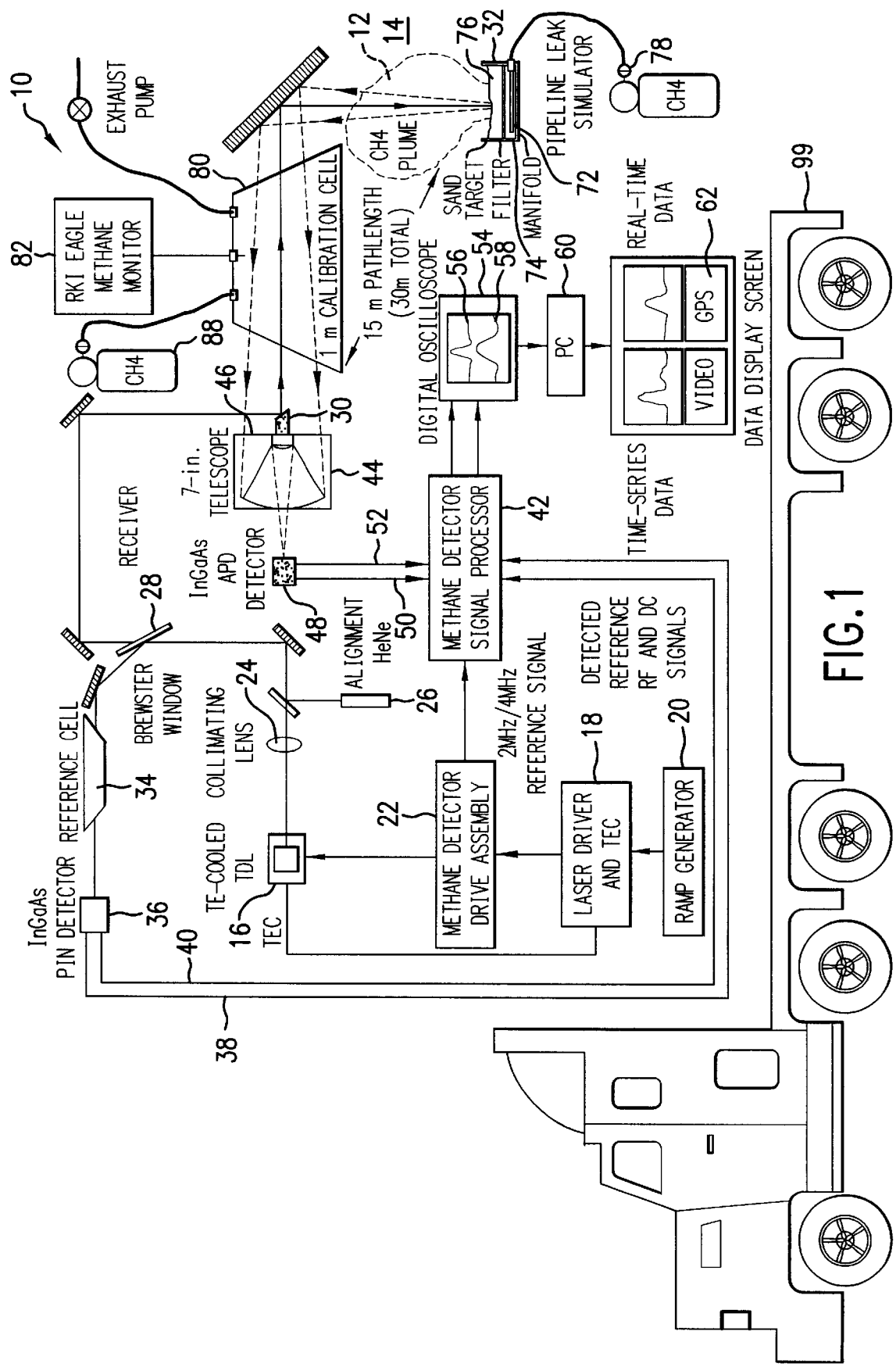
FIG. 1 is a functional block diagram of the preferred mobile TDL/FMS gas detection apparatus with reference cell.

With reference to FIG. 1, the preferred detection apparatus, generally 10, is used to detect the presence of a remote methane gas plume 12 in the atmosphere, generally 14. The apparatus 10 includes a source of generally monochomatic light issued by a distributed feedback tunable diode 16. The diode 16 is an InGaAs/InP type that emits light in the 1.65 $\mu$m band, which is the first overtone band of methane. The diode 16 is manufactured by Sensors Unlimited, Inc. This type of diode 16, although not emitting in the fundamental absorption band of methane (3.3 $\mu$m)

provides significantly greater power than the lead salt TDL's available for use in the 3.3 μm band.

Basic control of the diode 16 is provided by a Melles Griot laser diode/thermoelectric cooler controller 18. The controller 18 provides DC laser drive current and temperature control of the TDL to set and maintain the diode 16 emissions at the desired wavelength, 1.65 μm.

A ramp generator 20, manufactured by Stanford Research Systems, is connected to the controller 18 and thus adds to the drive current provided by the controller 18 a low current saw-tooth ramp signal (0.5 volt) at a relatively low repetition frequency of 1 kHz. This ramp signal sweeps the TDL 16 over a wavelength range of about 3 GHz, which is approximately twice the width of the atmospheric pressure-broadened absorption line width of the first overtone band of methane. As a result, the ramp signal sweeps the output of the TDL 16 so that a significant portion of the sweep occurs within the absorption line and a substantial portion of the sweep takes places outside the line. Sweeping at 1 kHz means that this type of sweep occurs 1,000 times per second.

The ramped drive current from the controller 18 is then fed into the methane detector drive assembly (MDDA) 22. The design and operation of such an MDDA 22 is well known to those of skill in the art. The MDDA 22 modulates the drive current with a 4 MHZ radio frequency signal. The MDDA 22 is then connected to the TDL 16 to drive it with the ramped and rf modulated drive current to yield sidebands displaced from the carrier frequency of the ramped drive current. The laser output from the TDL 16, including the carrier frequency and the upper and lower sideband signals displaced from the TDL 16 carrier wavelength by the modulation frequency, are thus swept across the absorption line of methane. As a result, an unbalance in the sideband signals will occur if an absorption is present. This unbalance yields a derivative line shape signature with an amplitude proportional to the gas concentration. As explained in the '511 patent, the amplitude of these sidebands is a Bessel function.

The frequency-swept and frequency-modulated laser output of the TDL 16 is then fed through a laser collimating lens, 24, and a helium neon alignment laser 26, and then through a brewster window 28. The helium neon alignment laser 26 emits light in the visible spectrum to provide a visible light source for alignment of the apparatus in a fashion well known in the art. The brewster window 28 directs most of the laser light toward the laser output mirror 30, which directs the laser light toward the target in the atmosphere, e.g., the sand ground 32. The brewster window 28 also directs a small amount of the laser light through methane gas reference cell or chamber 34. The laser light thus passes through the reference cell 34 to an InGaAs PIN photodetector/receiver 36. The PIN receiver 36 detects the laser light and outputs two signals. One signal is proportional to the quantity of the light incident on the detector and the other signal is proportional to the modulation frequency of the laser light incident on the detector. The method of arranging and operating the PIN detector 36 is well known to those skilled in the art.

The outputs 38, 40 of the PIN receiver 36 are connected to the reference channel signal inputs (not shown in detail) of a methane detector signal processor (MDSP) 42. The MDSP 42 contains demodulation circuits that are not shown and are well known to those skilled in the art. The MDSP 42 circuits (not shown) provide either first derivative (2 MHZ) or second derivative (4 MHZ) FMS signature information (derived from the first sideband or second sideband, respectively, as explained the '511 patent). Although not shown in FIG. 1, this information can be line-locked with the Melles Griot controller 18 in order to lock in the sweep of the TDL 16 of the desired absorption line of methane as described above. This wavelength control circuit logic can be installed in MDSP 42 and eliminate the need for the Melles Griot controller 18 and the ramp generator 20 by performing the functions of the controller 18 and ramp generator within the MDSP 42.

A seven inch F2.5 telescope 44 serves as the reflected light collector for the apparatus 10. The collector 44 is focused on the target 32, and the laser output mirror 32 is mounted adjacent the light entry-way 46 of the collector so that the laser emitted toward the target 32 is in alignment with the laser light back from the target 32 and received by the collector 44.

The telescope or collector 44 thus receives and focuses the reflected laser light on an InGaAs Avalanche Photo Diode (APD) detector 48. The APD photodetector 48 provides noise equivalent power (NEP) performance of approximately 0.1 $pW-Hz^{1/2}$. The APD photodetector 48 detects the RF (modulation) 50 and DC (photocurrent) 52 components of the reflected laser light in a fashion well known to those skilled in the art and provides two current outputs proportional to the modulation and photocurrent components. These outputs 50, 52 of the APD photodetector 48 are connected to the main signal inputs (not shown in detail) of the methane detector signal processor (MDSP) 42 in a fashion well known to those skilled in the art.

Accordingly, the sampling rate(s) of the detectors 48, 36 is the same as the ramp or saw-tooth frequency, 1 KHz. The detectors 48, 36 also have a bandwidth of 20 MHZ. The amount of modulation component detected by the PIN receiver 36 and the APD photodetector 48 are directly proportional to the total absorption along the laser beam path through the reference cell 34 and target 32 respectively. In addition, the amount of modulation component detected by the APD photodetector 48 is calibrated by the MDSP 42 circuitry based upon the distance of the apparatus 10 and particularly its output mirror 30 to the target 32. The MDSP 42 then combines the detected back scattered signal modulation component 50 with the reference modulation component from the MDSP 42, which cancel each other out when no absorption takes place along the path to or from the target 32. As explained in the '511 patent, when methane absorption does take place along the path to or from the target 32, the back scatter and reference modulation no longer cancel each other out, producing a derivative FMS signature or signal, thus indicating the presence of methane in the atmosphere along the path to or from the target 32.

The MDSP 42 provides signal conditioning electronics in order to optimize detection response or derivative FMS signal. The conditioning electronics include phase control, bandpass filtering, amplifiers, and signal level control circuits. Digital signal processing, DSP, such as Kalman filtering or matched filtering may be used, as further explained below. These components and their use are well known in the art.

The MDSP 42 then forwards the field and reference FMS signatures to a digital oscilloscope 54 for monitoring and digitizing the waveforms for observation and further processing. In the arrangement shown in FIG. 1, the top trace 56 on the oscilloscope represents the second derivative signature (4 MHZ) for the reference cell methane concentration, and the bottom trace 58 represents that second derivative signature for the field methane concentration detected by the laser light traveling through a methane plume 12 to and from the target 32. The difference in temporal shape between the reference and field FMS signatures is due to the relatively low pressure of the methane gas in the reference cell and its relatively narrow methane absorption line as compared to the atmospheric-pressure-broadening of the methane absorption line in the atmosphere.

The oscilloscope 54 provides signature data output, which then is input into a IBM-compatible personal computer (PC) 60 via a General Purpose Instrument Bus (GPIB) bus cable interconnecting GPIB ports in the oscilloscope 54 and the PC 60. Alternatively, the PC 60 may be a portable laptop computer with a standard, off-the-shelf digitizing card mounted inside the laptop.

Figure 2:
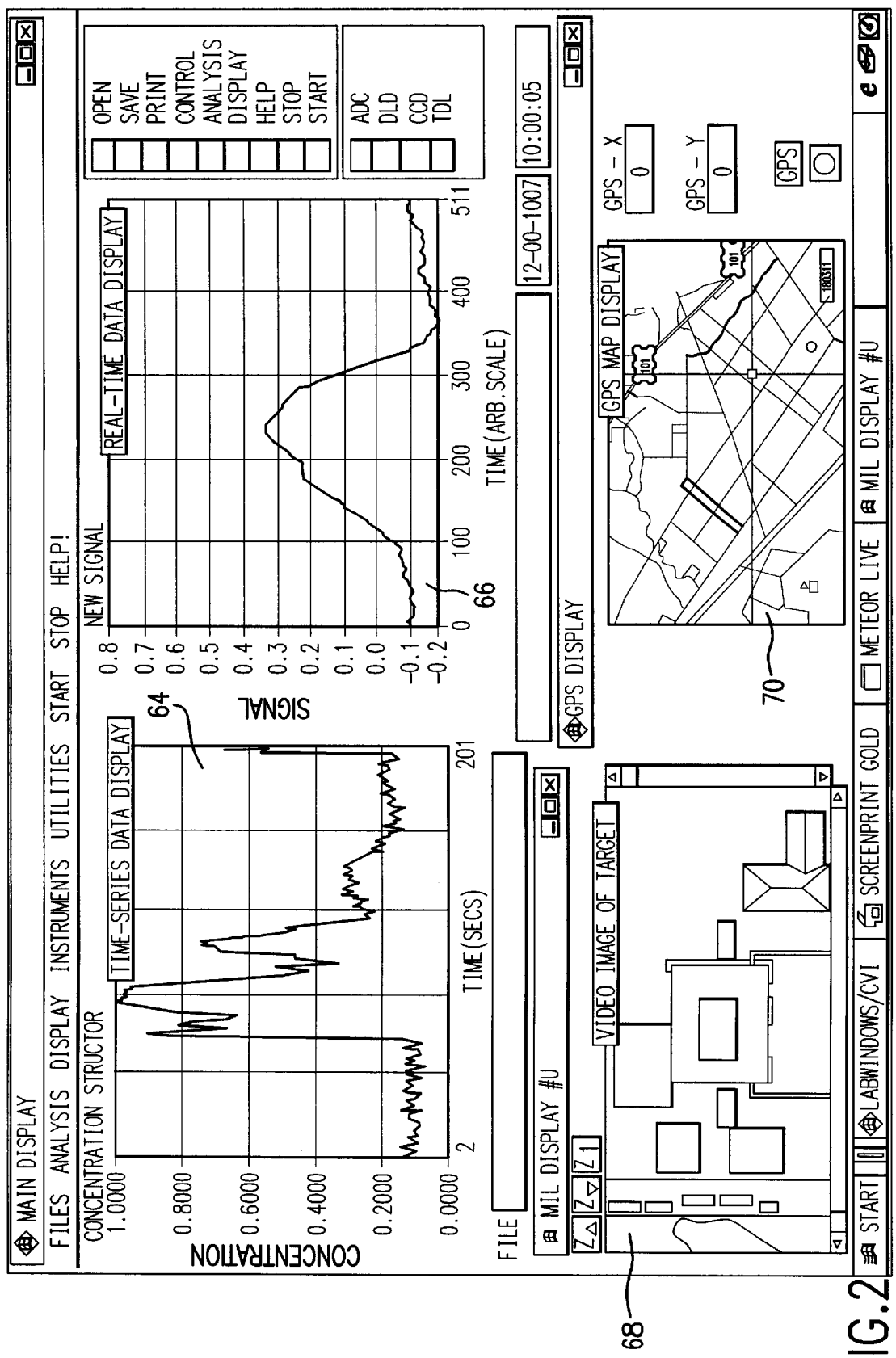
FIG. 2 is the video data display screen for remote methane leak detection by the preferred detection apparatus shown in FIG. 1.

The PC 60 has a video display 62. MICROSOFT LAB WINDOWS (TRADEMARK) software running on the PC 60 in a fashion well known in the art processes the signature data from the oscilloscope and provides a display of data such as shown in FIG. 2. With reference now to FIG. 2, the data display 62 includes a graph of time series data 64, which shows the concentration of methane in the atmosphere over time. The display also includes a real-time graph of the absorption line detection, if any is taking place, as is the case in the example shown in FIG. 2. The data display 62 further includes (i) a real-time target area 68 display being interrogated by the LIDAR apparatus 10 of FIG. 1, and (ii) a global positioning satellite (GPS) controlled presentation 70 of the location shown in the real-time target area display 68.

Referring back to FIG. 1, the apparatus 10 is preferably mounted on a mobile platform 99 such as a small truck or sports utility vehicle. The apparatus weighs about 100 lbs. and occupies about 6 cu. ft. within the vehicle. The apparatus is thus uniquely quite mobile and useable for the remote detection of plumes of methane in the atmosphere.

EXAMPLES

In order to test the apparatus 10, remote gas leak simulation was effected by disseminating methane through a manifold 72 over a 3 sq. inch area under a paper filter 74 underlying, and separating the manifold 72 from, a sand target 76 about one half inches deep. The methane needle valve 78 was opened for varying periods of time in order to simulate large and small gas leaks in the 10 to 300 p.p.m. range. The display shown in FIG. 2 is an example of the data collected during one such simulated gas leak.

In order to calibrate the response of the apparatus 10, a 10 inch diameter, 1 meter long sample chamber or reference cell 80 can be placed in the path of the laser light emitted from the output mirror 30. A pre-calibrated RKI EAGLE (TRADEMARK) methane monitor 82 is connected to the chamber in a manner well known to those skilled in the art. The methane monitor 82 provides an independent measurement of methane concentration in the cell as function of time during the test.

Figure 3:
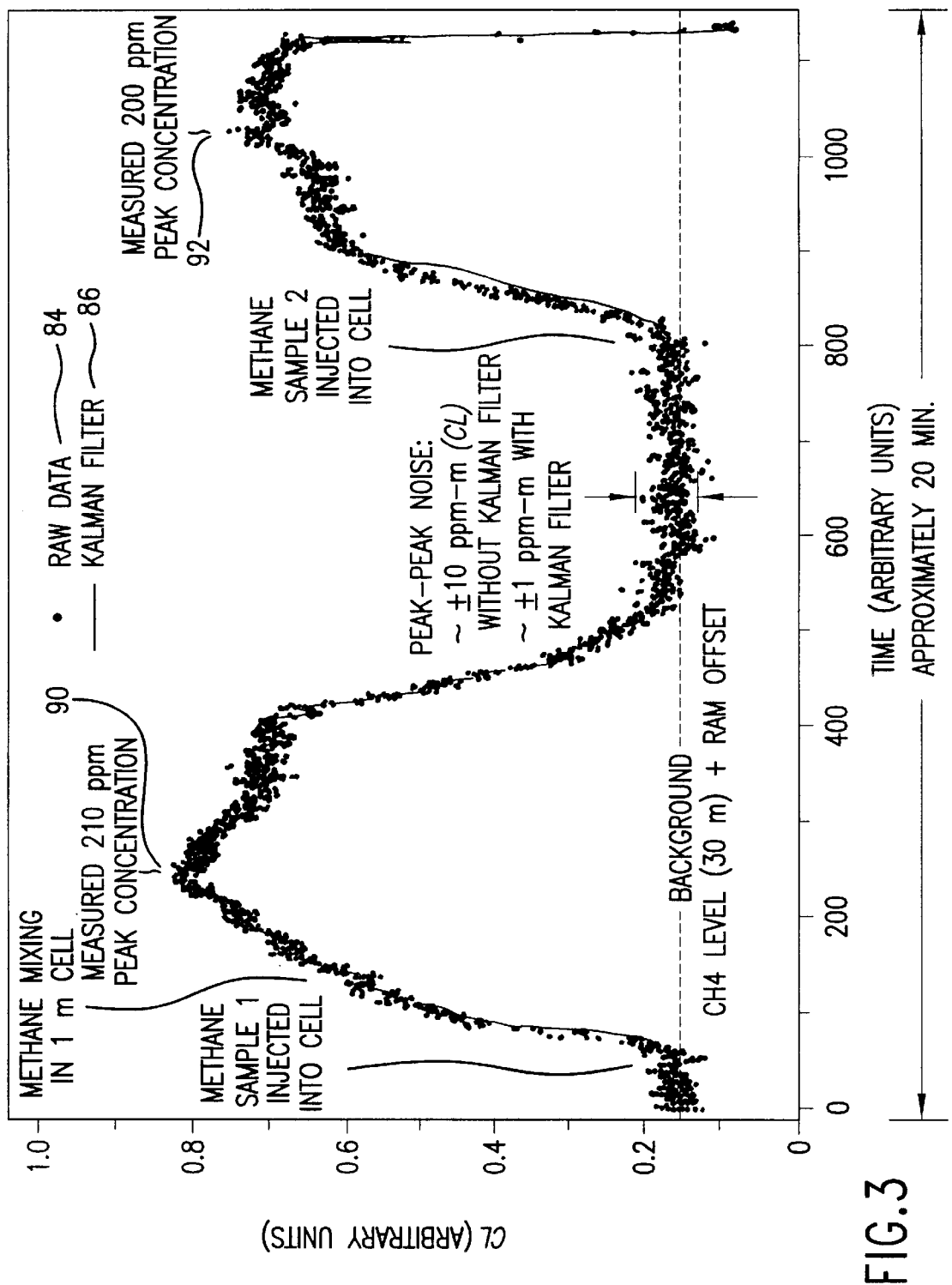
FIG. 3 is the calibration monitor display screen of the preferred detection apparatus shown in FIG. 1.

The PC 60 output to a standard color printer (not shown) provides a calibration graph such as shown in FIG. 3, including both raw 84 and Kalman-filtered 86 TDL LIDAR data. This output and printout such as shown in FIG. 3 is generated through LAB WINDOWS (TRADEMARK) software running on the PC in a fashion well known to those skilled in the art.

Since the sample chamber 80 is 1 meter in length, the FMS signal detected by the ACP photodetector 48 is a one meter, path integrated measurement. Accordingly, the signal levels recorded when the methane concentration in the chamber 80 is at equilibrium (several minutes after dispersion of the gas into the chamber 80) correspond to the known concentration of the methane in the chamber 80 as indicated by the methane monitor 82 (210 p.p.m.-m in this instance). A linear CL division scale is constructed and provided on the graph shown in FIG. 3 between the limits of the reference path integrated concentration level (CL, 210 p.p.m.-m) and the background CL level measured prior to injection of the methane into the chamber 80. With Kalman filtering of the data, the minimum detection is in the range of less than 10 p.p.m.-m, and without Kalman filtering, the minimum detection is in the range of 10–20 p.p.m.-m. Another DSP technique that can improve the detection performance significantly is the use of matched filtering. Matched filtering requires that a detection technique be used such as FMS derivative detection, that provides a well characterized temporal signature of the absorption line feature being detected. The FMS detection scheme in the present design provides second derivative absorption line features that are ideally suited for this application. Matched filtering works by correlating the noisy signal with a template representing the time signal shapes. It is a statical approach for finding weak signals under fairly general assumptions about the noise statistics.

In the calibration test shown in FIGS. 1 and 3, at first the sample chamber 80 contained no methane. After recording several minutes of background data, a trace amount of methane was injected into the chamber 80 by a calibration methane source 88. As the gas dispersed into and reached equilibrium within the chamber 80, the ADP photodetector 48 detected the absorption and the results are indicated in the first peak 90 shown in the calibration graph 90 in FIG. 3. Since the methane monitor 82 indicated a concentration of 210 p.p.m. of methane in the sample chamber 80 at the time of the occurrence of the first peak 90 of FIG. 3, the operator could see that the output of the display screen 62 correlated quite well with the methane concentration measured by the methane monitor 82.

In the example shown in FIG. 3, the operator performed a second test after several minutes, and the display screen 62 indicated the results by the second peak 92. Once again, the display screen 62 indicated a high degree of correlation between the concentration of methane measured in the sample chamber 80 (200 p.p.m.) and that shown in the display screen 62.

It can thus be seen that the applicants' preferred embodiments provide a particularly effective and yet economical and mobile method and apparatus for the remote detection of gas, particularly methane, in the atmosphere. Once set up, the apparatus can run unattended as the vehicle containing the apparatus moves at typical operational speeds of 20 to 30 m.p.h. The preferred LIDAR apparatus 10 uses a single TDL, and it provides continuous wave operation. It also provides significant self-calibration by means of the integral reference cell 80.

It is to be understood that the foregoing is a detailed description of the preferred embodiments. The scope of the applicants' invention, however, is to be determined by reference to the following claims.

We claim:

1. A method of remotely detecting a particular gas dispersed in the atmosphere, the dispersed gas being of the type that absorbs light at frequencies within an absorption line range for the dispersed gas in the atmosphere, the method comprising the steps of:

driving a source of generally monochromatic light by a laser drive to provide a carrier output at a predetermined frequency;

frequency modulating the laser drive with a modulation frequency to generate at least one frequency modulated sideband signal in the output of the light source; and adding to the laser drive a ramp frequency to scan the light source and the sideband signal across a scan range including at least a portion of the absorption line range;

directing at least a test portion of the ramped and modulated light toward an uncooperative target;

collecting light reflected from the uncooperative target and directing it toward a first detector to generate at least one test signal based on the degree of attenuation of the sideband signal by the dispersed gas; and generating an output indicative of an amount of the dispersed gas in the atmosphere, if any, based on the at least one test signal.

2. The method of claim 1 wherein: (i) the directing step also includes directing a reference portion of the ramped and modulated light through a reference gas cell containing a reference amount of the particular gas and then to a second detector to generate at least one reference signal based on the degree of attenuation of the sideband signal by the reference amount of the particular gas; and (ii) the generating step includes mixing the test signal with the reference signal to provide a combined signal indicative of the degree of attenuation of the first sideband signal by the gas in the reflected light.

3. The method of claim 1 wherein: (i) the directing step also includes directing a calibrating portion of the ramped and modulated light through a calibrating amount of the particular gas in a calibrating cell, (ii) the collecting step also includes collecting the calibrating light portion after passage through the calibrating gas cell to generate at least one calibrating signal based on the degree of attenuation of the sideband signal by the calibrating amount of the particular gas in the calibrating gas cell, and (iii) the generating step includes calibrating the output based on the calibrating signal.

4. The method of claim 2 wherein: (i) the directing step also includes directing a calibrating portion of the ramped and modulated light through a calibrating amount of the particular gas in a calibrating cell, (ii) the collecting step also includes collecting the calibrating light portion after passage through the calibrating gas cell to generate at least one calibrating signal based on the degree of attenuation of the sideband signal by the calibrating amount of the particular gas in the calibrating gas cell, and (iii) the generating step includes calibrating the output based on the calibrating signal.

5. The method of claim 1 wherein, in the adding step, the ramp current and frequency are predetermined so that the scan range is twice the width of the atmosphere-pressure broadened absorption line width of the particular gas.

6. The method of claim 2 wherein, in the adding step, the ramp current and frequency are predetermined so that the scan range is twice the width of the atmosphere-pressure broadened absorption line width of the gas.

7. The method of claim 3 wherein, in the adding step, the ramp current and frequency are predetermined so that the scan range is twice the width of the atmosphere-pressure broadened absorption line width of the gas.

8. The method of claim 4 wherein, in the adding step, the ramp current and frequency are predetermined so that the scan range is twice the width of the atmosphere-pressure broadened absorption line width of the gas.

9. A method of remotely detecting a particular gas dispersed in the atmosphere, the particular gas being of the type that absorbs light at frequencies within an absorption line range for the particular gas in the atmosphere, the method comprising the steps of:

A. applying direct current to a tunable diode laser in order to generate a source of generally monochromatic light driven to provide a carrier output frequency within the absorption line range;

B. frequency modulating the output of the laser drive with a modulation frequency to generate at least one upper sideband signal and one lower sideband signal; and C. adding to the laser drive a ramp frequency to scan the sideband signals across a scan range so that at least one of the sideband signals scans at least a portion of the absorption line range;

D. directing the ramped and modulated light toward an uncooperative target;

E. collecting the ramped and modulated light reflected from the uncooperative target toward a first detector to generate at least one test signal based on the degree of attenuation of at least the one sideband signal by the particular gas; and F. generating an output indicative of an amount of the particular gas in the atmosphere, if any, based on the at least one test signal.

10. The method of claim 9 wherein: (i) the directing step also includes directing a reference portion of the ramped and modulated light through a reference gas cell containing the particular gas and then through a second detector to generate at least one reference signal based on the degree of attenuation of at least the one sideband signal by the particular gas in the reference gas cell; and (ii) the generating step includes mixing the test signal with the reference signal to provide a combined signal indicative of the degree of attenuation of the one sideband signal by the particular gas.

11. The method of claim 9 wherein: (i) the directing step also includes directing a calibrating portion of the ramped and modulated light through a calibrating gas cell, (ii) the collecting step also includes collecting the calibrating light portion after passage through the calibrating gas cell to generate at least one calibrating signal based on the degree of attenuation of the one sideband signal by a calibrating amount of particular gas in the calibrating gas cell, and (iii) the generating step includes calibrating the output based on the calibrating signal.

12. The method of claim 10 wherein: (i) the directing step also includes directing a calibrating portion of the ramped and modulated light through a calibrating gas cell, (ii) the collecting step also includes collecting the calibrating light portion after passage through the calibrating gas cell to generate at least one calibrating signal based on the degree of attenuation of the one sideband signal by a calibrating amount of the particular gas in the calibrating gas cell, and (iii) the generating step includes calibrating the output based on the calibrating signal.

13. The method of claim 9 wherein, in the adding step, the ramp current and frequency are predetermined so that the scan range is twice the width of the atmosphere-pressure broadened absorption line width of the particular gas.

14. The method of claim 10 wherein, in the adding step, the ramp current and frequency are predetermined so that the scan range is twice the width of the atmosphere-pressure broadened absorption line width of the particular gas.

15. The method of claim 11 wherein, in the adding step, the ramp current and frequency are predetermined so that the scan range is twice the width of the atmosphere-pressure broadened absorption line width of the gas.

16. The method of claim 12 wherein, in the adding step, the ramp current and frequency are predetermined so that the scan range is twice the width of the atmosphere-pressure broadened absorption line width of the gas.

17. The method of claim 1 wherein, in the driving step, the carrier output frequency is predetermined to be within an overtone absorption line of the particular gas.

18. The method of claim 9 wherein, in the driving step, the carrier output frequency is predetermined to be within an overtone absorption line of the particular gas.

19. The method of claim 1 wherein, in the adding step, the ramp frequency scans across the scan range so that the one sideband signal scans within the absorption line range and the other sideband signal scans partially outside the absorption line range.

20. The method of claim 9 wherein, in the adding step, the ramp frequency scans across the scan range so that the one sideband signal scans within the absorption line range and the other sideband signal scans partially outside the absorption line range.

21. The method of claim 1 wherein the directing step includes moving the light source.

22. The method of claim 9 wherein the directing step includes moving the light source.

\* \* \* \* \*